United States Patent [19]

Liu

[11] Patent Number: 6,088,109
[45] Date of Patent: Jul. 11, 2000

[54] SYSTEM FOR DETECTING THE PRESENCE OF DEPOSITED METALS ON SOLDERING POINTS OF AN INTEGRATED CIRCUIT BOARD SUBSTRATE

[75] Inventor: Pai-Chou Liu, Kaohsiung, Taiwan

[73] Assignee: Advanced Semiconductor Engineering, Inc., Kaohsiung, Taiwan

[21] Appl. No.: 09/159,689

[22] Filed: Sep. 24, 1998

[51] Int. Cl.[7] ................................................. G01B 11/00
[52] U.S. Cl. ..................... 356/376; 356/394; 356/237.1
[58] Field of Search ................................. 358/518, 350; 356/376, 394, 237.1, 237.2, 237.5, 388, 390, 445, 448

[56] References Cited

U.S. PATENT DOCUMENTS

| | | | |
|---|---|---|---|
| 5,166,985 | 11/1992 | Takagi et al. | 356/237 |
| 5,245,671 | 9/1993 | Kobayashi et al. | 356/418 |
| 5,296,945 | 3/1994 | Nishikawa et al. | 358/518 |
| 5,343,386 | 8/1994 | Barber | 358/350 |
| 5,450,204 | 9/1995 | Shigeyama et al. | 356/378 |
| 5,686,994 | 11/1997 | Tokura | 356/394 |
| 5,760,893 | 6/1998 | Raymond | 356/237 |
| 5,774,224 | 6/1998 | Kerstens | 356/394 |
| 5,903,353 | 5/1999 | Raymond | 356/376 |

OTHER PUBLICATIONS

David W. Capson and Sai–Kit Eng, "A Tiered–Color Illumination Approach for Machine Inspection of Solder Joints", IEEE Transactions on Pattern Analysis and Machine Intelligence, vol. 10, No. 3, May 1988, pp388–391, May 1988.

*Primary Examiner*—Frank G. Font
*Assistant Examiner*—Roy M. Punnoose

[57] ABSTRACT

A system for detecting deposited metals on soldering points of an integrated circuit board substrate, a light source, a charge coupled device camera, and a computer. The camera captures an image of the substrate of a ball grid array integrated circuit board and converts the image into a digital image signal. The dot matrix image is transmitted to the computer for analysis by software to examine a conformity index between the image on the substrate to be detected and the image of a reference substrate, thereby providing an automatic detecting function.

11 Claims, 6 Drawing Sheets

SYSTEM FOR DETECTING THE PRESENCE OF DEPOSITED METALS ON SOLDERING POINTS OF AN INTEGRATED CIRCUIT BOARD SUBSTRATE

BACKGROUND OF THE INVENTION

1. Field of the Invention

The present invention relates to a detecting device for deposited metals on soldering points on a substrate of an integrated circuit board, particularly a ball grid array (BGA) integrated circuit (IC) board substrate, to thereby detects defect with respect to the lack of deposited metals for soldering points on the substrate.

2. Description of the Related Art

A ball grid array integrated circuit (BGA IC) packaging method is a newly developed method for ICs with a quantity of pins and is suitable for packaging ultra-large scale integration (ULSI) produced by submicron solution. In such a packaging method, divided single chips are secured on the substrate of the BGA IC, and a package encapsulant is provided to enclose the IC chips projecting beyond the surface of the substrate.

The soldering points on the substrate of the above-mentioned BGA IC form a ball grid array. A deposited metal is formed in advance for each soldering point in order to allow easy subsequent formation of a tin ball on each soldering point. If the deposited metal is not properly deposited, the tin ball tends to be disengaged from the substrate and thus results in a defective product. The packaging process is the last process in integrated circuit manufacture. Disengagement of the tin ball causes a waste in production, as the signal function of the chips on the IC will be adversely affected. The defect index can be largely reduced if the deposited metals that act as tin ball pads can be detected in advance.

Conventionally, the deposited metals on the soldering points on the BGA IC are detected by human vision with an aid of a magnifier, which is slow and apt to have misjudgment due to eye-strain or personnel error.

As a result of progress in computer and image input device and technique therefor, detection by computer analysis in the images of computer elements has been utilized in industry, and an example of which is disclosed in Taiwan Patent Publication No. 305940 that discloses an apparatus and method for detecting integrated circuits. In this Taiwan Patent Publication No. 305940, light beams from a light base are switched to illuminate the integrated circuit elements. The shadows thus generated are reflected with a number of lenses to capture the shadow images of the IC elements. The shadow images of the pins of the IC elements are transmitted to the computer for analysis. This, the image identifying technique by computer is used to replace eye detection and applied to detect deposited metals for soldering points on the substrate of BGA IC.

SUMMARY OF THE INVENTION

It is a primary object and advantage of the present invention to utilize computer detection for determining the presence of deposited metals on soldering points on a substrate of an integrated circuit board and replace conventional eye detection plagued by low detecting speed and unavoidable error.

In order to achieve the above object, the device of present invention utilizes a light source, a charge coupled device for receiving light beams, and a computer. The image of each soldering point of the substrate of an integrated circuit board is captured and converted into a digital image signal. The image of each soldering point to be detected on the inspected substrate is compared with a reference image of a qualified substrate by computer software analysis. The inspected substrate is acceptable if the difference between the compared images is smaller than a predetermined value. Otherwise, the substrate is defective and rejected. The detection result is outputted and thus obtains an automatic detection effect.

In accordance with the present invention, a detecting device is provided for deposited metals on soldering points of a substrate of an integrated circuit board. The detecting device comprises:

a light source provided on top of a substrate to be detected to provide illumination to the substrate to be detected, an image receiving element mounted on top of the substrate to be detected for receiving light beams reflected from the substrate to be detected and outputting a digital image signal of an image of the substrate to be detected formed by the light means, and an image processing device including an input and an output for signals, a memory for storing a reference image of a qualified substrate, and a central processing unit, the image processing device receiving the digital image signal from the image receiving element, the central processing unit comparing the image of the substrate to be detected and the reference image stored in the memory to judge whether the substrate to be detected is a qualified one, and the result of the judgment being outputted by the output.

The digital image is represented by a dot matrix of pixels. A standard for judging whether the substrate to be detected is based on a conformity index between the image of the substrate to be detected and the reference image of the qualified substrate. In an embodiment of the invention, an area of pixels of a soldering point on the substrate to be detected is selected as a reference for judgment, and a reference value is set to provide a reference of the conformity between the image of the substrate to be detected and the reference image of the qualified substrate. The substrate to be detected is judged as a qualified one if the conformity index is greater than the reference value. The reference value is changeable and ranges from 50% to 100%. Detection of the deposited metals may also be based on the colors of the deposited metals.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
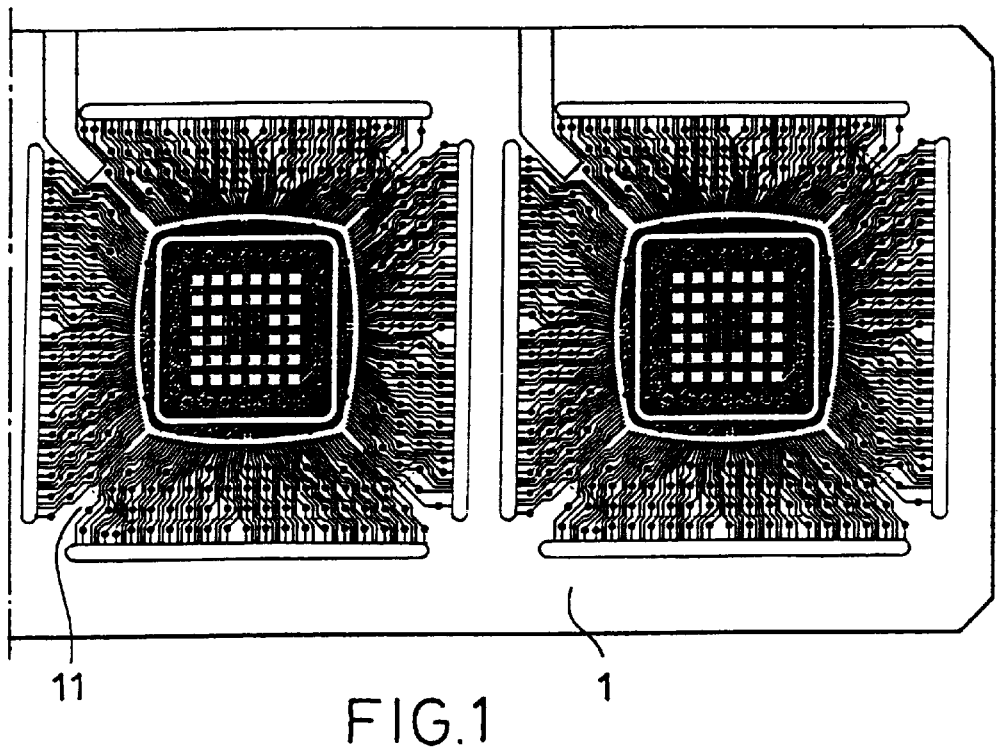
FIG. 1 is a top view of an upper side of a substrate of a ball grid array integrated circuit (BGA IC) board.
Figure 2:
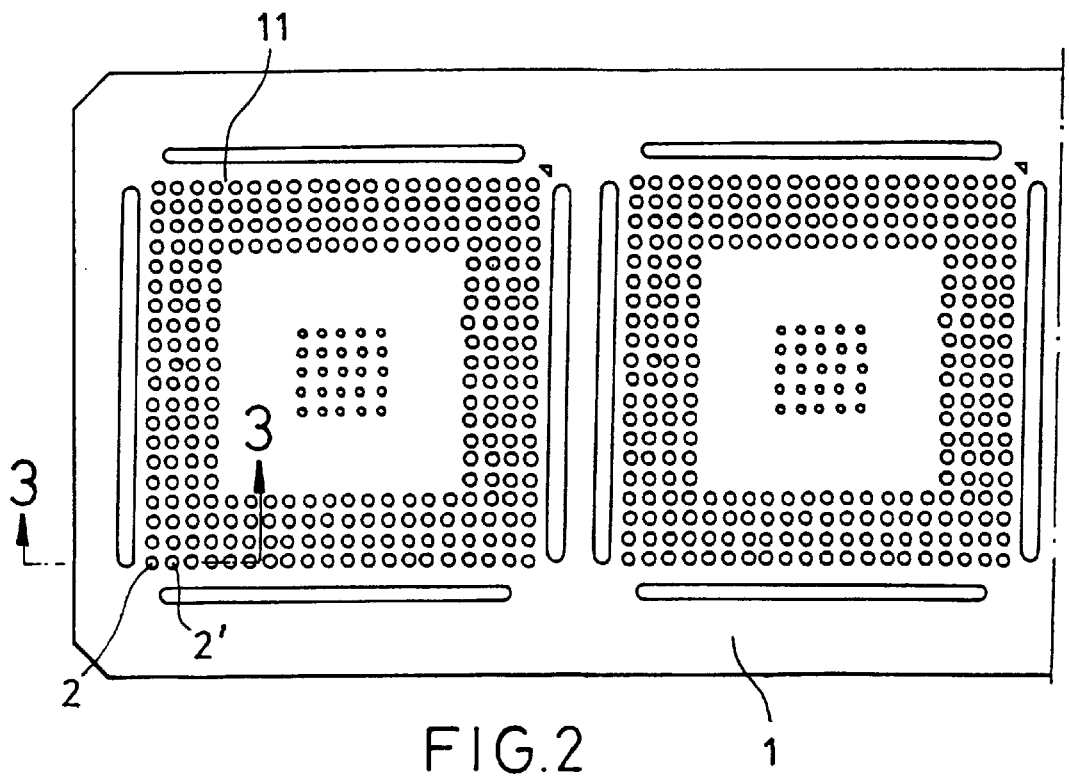
FIG. 2 is a bottom view of the BGA IC board.

FIG. 1 is a top view (the so-called "finger area") of a substrate 11 of a ball grid array (BGA) integrated circuit (IC) board to be detected by the detecting device in accordance with the present invention. The pattern shown in FIG. 1 is the layout of the printed circuit board, a portion of which is used as an area for deposited metals for soldering points to allow connection with IC chips (not shown). In actual manufacture, several substrates 11 are manufactured as a substrate set 1 for mass production FIG. 2 illustrates a bottom view (the so-called "tin ball area") of the BGA IC board 11, in which each circle represents a soldering point 2.

Figure 3:
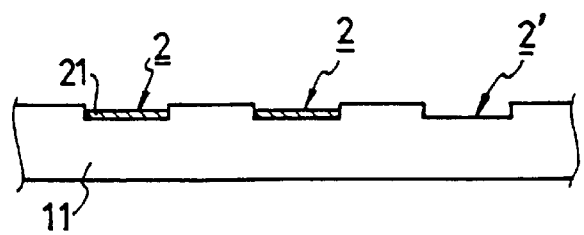
FIG. 3 is a sectional view taken along line 3—3 in FIG. 2.
Figure 4:
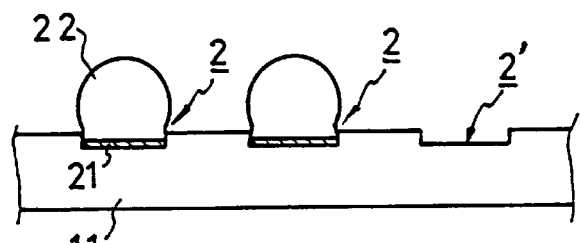
FIG. 4 is a sectional view similar to FIG. 3, illustrating formation of tin balls.

FIG. 3 is a section of the substrate 11 of the BGA IC board prior to formation of tin balls 22. A soldering point 2 has a deposited metal 21 therein, while a soldering point 2 is formed without a deposited metal 21 therein. The deposited metal 21 may serve as a pad for a tin ball 22 to provide a reliable bonding effect between the tin ball and the substrate 11 to thereby prevent disengagement of the tin ball. FIG. 4 illustrates a section of substrate 11 of the BGA IC board, in which tin balls 22 are formed on the associated tin ball pads 21 (i.e., the deposited metals). At soldering point 2', i.e., without the tin ball pad 21, a tin ball cannot be bonded to the substrate 11. This causes a break in the circuit at the soldering point 2' and thus results in a defective IC product made from the substrate 11.

Figure 6:
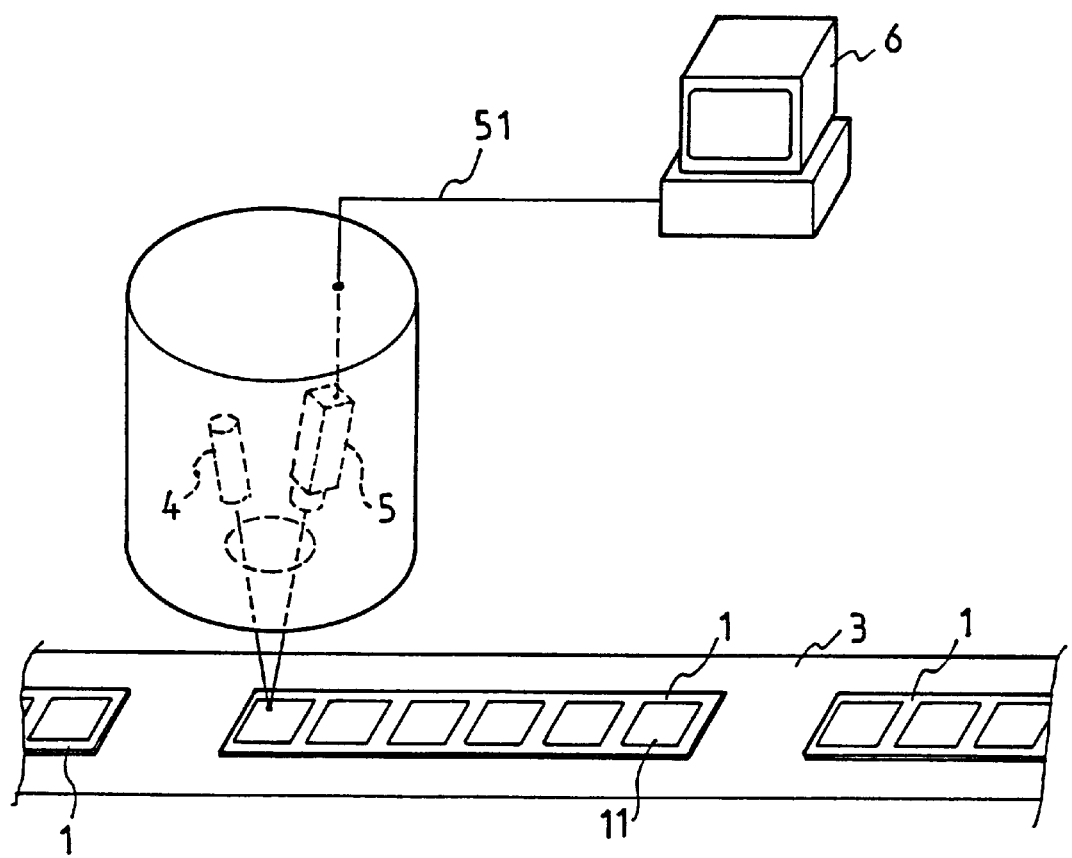
FIG. 6 is a schematic perspective view illustrating a detecting device for the substrate.

In order to avoid packaging of defective BGA IC board substrates 11, the defective substrates must be detected in advance. FIG. 6 is a schematic view of the detecting device for substrates in accordance with the present invention. As shown in this figure, the detecting device includes a platform 3, a light source 4, a charge coupled device (CCD) camera 5, and a computer 6.

The substrate set I consisting of a number of substrates 11 is securely placed on the platform 3 and conveyed by the platform to a predetermined location below the light source 4 and the CCD camera 5.

Figure 5:
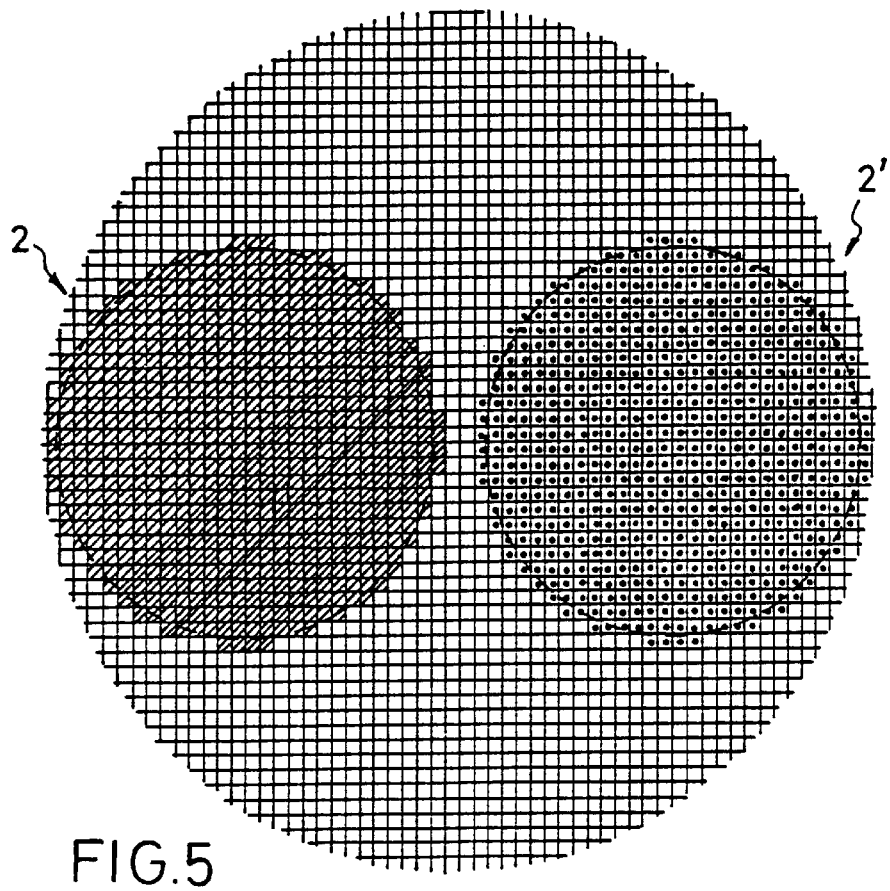
FIG. 5 is a dot matrix view of two soldering points on the bottom side of the BGA IC.

The substrate set I is illuminated by the light source 4 and the CCD camera 5 receives an image formed by the reflective light. The CCD camera 5 includes digital electronic elements that may convert the image into digital image information (FIG. 5). Other types of photo-detecting devices (e.g., scanners) that may receive image and output digital data of the image can be used.

The above-mentioned image information may be a conventional dot matrix image data for digital image processing. The image diagram is divided into a dot matrix of pixels in two dimensions according to solution requirement. Each pixel is then given a specific value representing specific information of the pixel. For example, "1" may represent "black" and "0" may represent "white" for a black-and-white image. The information in digital form is transmitted to an input port (not shown) of the computer 6 via a transmitting line (51) to proceed with software analysis of the image. The computer may be a personal computer or other types of microprocessors with micro-processing units (i.e., a device with a central processing unit, memory, and input/output port).

FIGS. 7 to 10 illustrate the procedure for processing images in accordance with the present invention.

Figure 7:
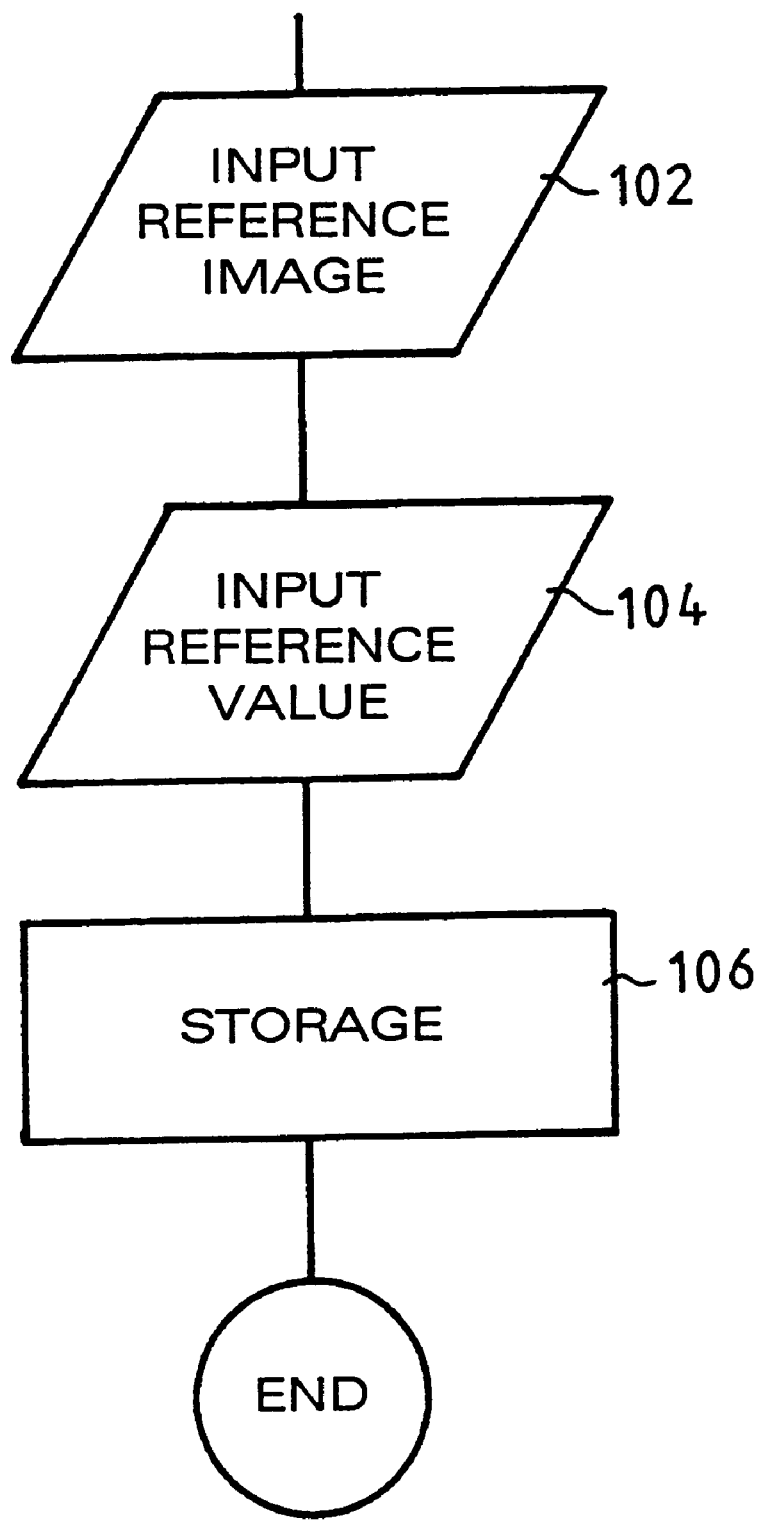
FIG. 7 is a flowchart illustrating an input procedure of a reference image and a reference value.

As shown in FIG. 7, firstly, an image of a qualified substrate (reference substrate) is inputted into the computer as a reference image (Step 102). Then, a value is inputted into the computer as a reference value for deciding whether the substrate detected is a qualified one (Step 104). The data of the reference image and the reference value are stored in a memory of the computer (Step 106).

Figure 8:
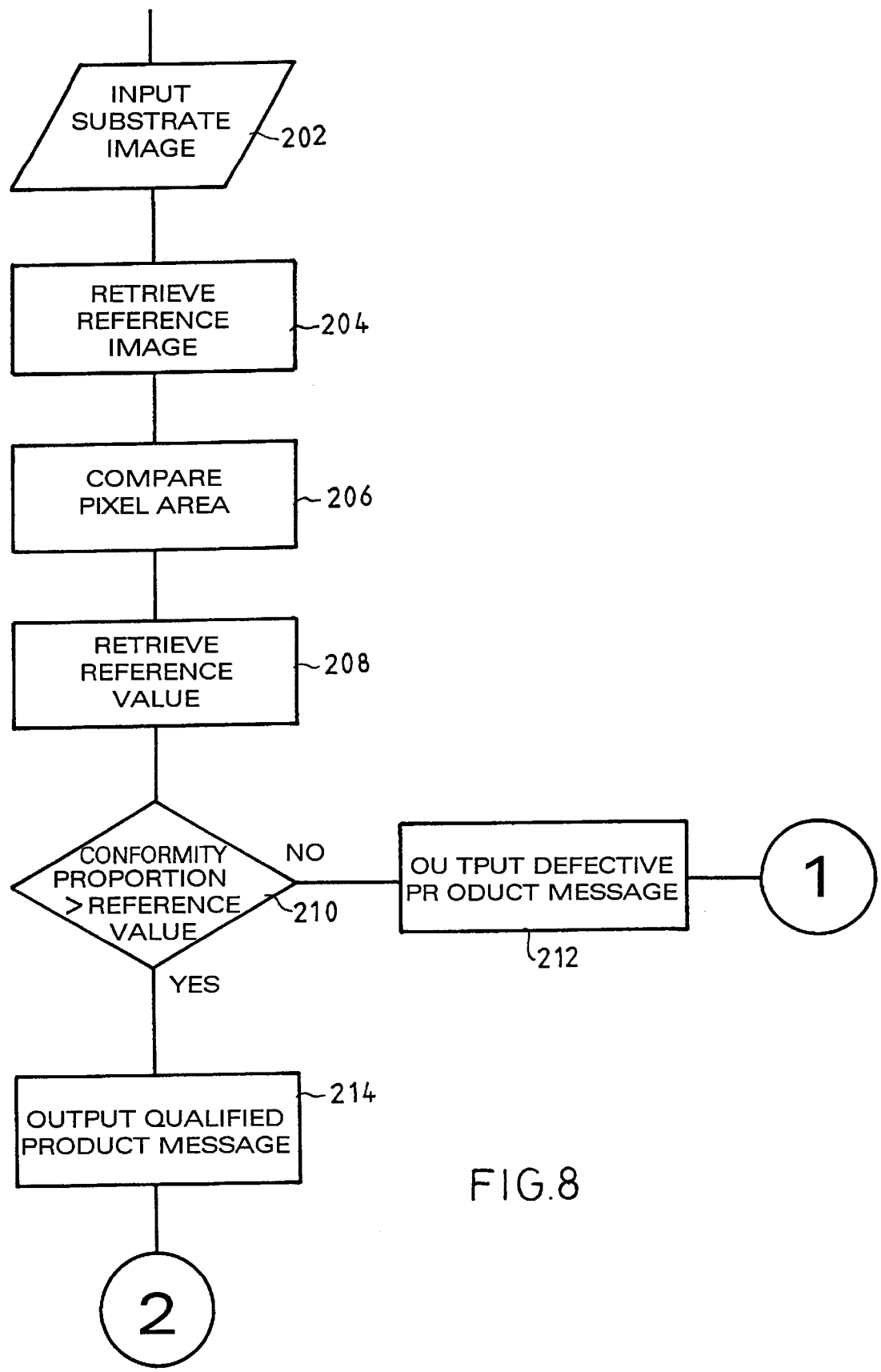
FIG. 8 is a flowchart illustrating comparison of an input image and the reference image.
Figure 9:
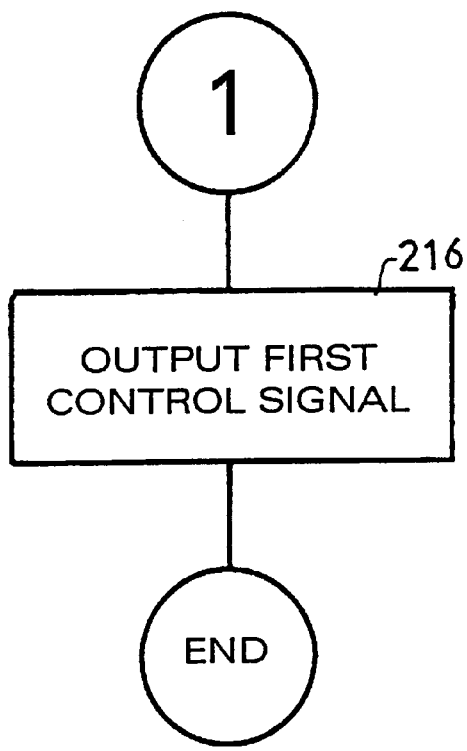
FIG. 9 is a diagram illustrating a subsequent control step.
Figure 10:
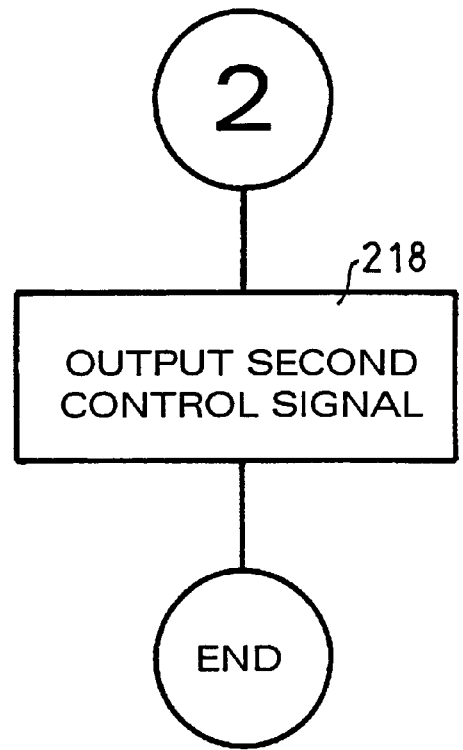
FIG. 10 is a diagram illustrating anther subsequent control step.

FIG. 8 illustrates a flowchart for comparing a substrate to be detected with the reference substrate. Firstly, the image data of the substrate to be detected is inputted into the computer (Step 202). Then, the reference image is retrieved from the memory (Step 204). The pixel area of the substrate to be detected is compared with the pixel area of the reference image (Step 206) to obtain a conformity index. The reference value is then retrieved from the memory (Step 206). Next, the conformity index between the two pixel areas is compared with the reference value (Step 210). If the conformity index is greater than the reference value, a message is outputted to indicate that the substrate is a qualified one (Step 214). To the contrary, if the conformity index is smaller than the reference value, a message is outputted to indicate that the substrate is a defective (disqualified) one (Step 212). FIG. 9 illustrates a subsequent step of outputting a first control signal (Step 216), while FIG. 10 illustrates a subsequent step of outputting a second control signal (218), which will be described later.

The processing procedure of the images is described as follows.

Input of the image data of the reference substrate and the image data of the substrate detected is accomplished by a CCD camera 5, as mentioned above. Each pixel of the digital image of the substrate detected is compared with a corresponding pixel of the reference image of the reference substrate. As the color of a soldering point 2 with a deposited metal differs from that of a soldering point 2' without a deposited metal, the color of each pixel of the digital image of the substrate detected is compared with the color of the corresponding pixel of the reference substrate. The color difference may be used as a reference for determining whether the substrate detected is acceptable or disqualified. In addition, different deposited metals have different colors in the image thereof As a result, comparison can also occur if the substrate has deposited metals of different material.

There are many options for comparison of the images. For example, in an area of the soldering point 2 of the detected substrate that has the same color as an area of a corresponding soldering point of the reference substrate, the length of the contour, the maximum vertical length, the maximum horizontal length, or the pixel area can be selected for comparison purposes. In this embodiment, the pixel area is selected as the standard for proceeding with comparison. More specifically, in an area of the soldering point 2 of the detected substrate that has the same location as an area of the corresponding soldering point of the reference substrate, a proportion of the total area of the pixels of the image of the detected substrate that have the same color as the corresponding pixels of the reference substrate to the overall area of the soldering point 2 is calculated and recorded as the conformity index.

The conformity index is compared with the reference value retrieved from the memory to determine whether the detected soldering point has a deposited metal. In this embodiment, the reference value is set as 75%. Namely, if the conformity index of the area of the detected soldering point 2 that has the same color as a corresponding area of corresponding soldering point of the reference substrate exceeds 75% (relative to the overall area), the soldering point 2 is determine as having a deposited metal. To the contrary, the soldering point 2 is judged as having no deposited metal. As the conformity index approaches 100% when the soldering point 2 has a deposited metal or approaches 0 when the soldering point 2 has no deposited metal, the reference value may be in a range of 50%~100% for correct detection.

The result of the judgement (a signal that indicates the detected substrate is a qualified product or defective product) is outputted via the output port (not shown) of the computer to a peripheral device, e.g., an indication lamp, a display, a siren, or other audio, photoelectric, or electromechanical elements. Control signals can also be outputted. As shown in FIG. 9, a first control signal may be sent to convey the qualified product to one place, while a second control signal (FIG. 10) may be sent to convey the defective product to another place.

According to the above description, it is appreciated that the detecting device in accordance with the present invention can be used to replace eye detection. The detecting device of the present invention may automatically, and rapidly detect the deposited metals on the soldering points on the substrate of an IC board without error.

Although the invention has been explained in relation to its preferred embodiment, it is to be understood that many other possible modifications and variations can be made without departing from the spirit and scope of the invention as hereinafter claimed.

What is claimed is:

1. A computerized system for detecting the presence of deposited metals on soldering points of a substrate of an integrated circuit board, the detecting system comprising:

a light source adapted to positioned above the substrate to provide illumination of the soldering points;

an image receiving element adapted to be mounted above the substrate for receiving light beams reflected from the substrate as a result of said illuminations and outputting a digital image signal of an image of the substrate formed by the beams; and an image processing device including an input and an output for signals, a memory storing a predetermined reference image of an acceptable substrate, and a central processing unit, the image processing device receiving the digital image signal from the image receiving element, the central processing unit having a program for comparing the image of the substrate and the reference image stored in the memory to determine whether the substrate to be detected is acceptable, and the result of the determination being outputted by the output.

2. The detecting system as claimed in claim 1, wherein the digital image is represented by a dot matrix of pixels.

3. The detecting system as claimed in claim 2, wherein said program includes a standard having a conformity index for determining whether the image of the substrate to be detected and the reference image of an acceptable substrate are in conformity with each other.

4. The detecting system as claimed in claim 3, wherein an area of pixels of a soldering point on the substrate to be detected is selected as a reference for the determination, and a reference value is set to provide a reference of the conformity between the image of the substrate to be detected and the reference image of the acceptable substrate, wherein the substrate to be detected is determined as a qualified one if the conformity index is greater than the reference value.

5. The detecting system as claimed in claim 4, wherein the reference value is changeable and ranges from 50% to 100%.

6. The detecting system as claimed in claim 3, wherein detection of the deposited metals is based on the colors of the deposited metals.

7. A method for determining the acceptability of a manufactured ball grid array integrated circuit board substrate, comprising the steps of illuminating:

a surface of the substrate to provide illumination of soldering points thereon;

creating a digital image signal representative of an image of said substrate formed as a result of said illumination;

comparing the digital image signal with a reference image stored in a computer memory to determine whether the manufactured substrate satisfies predetermined acceptance criteria.

8. The method of claim 7, wherein the comparing steps are made utilizing a computer program including a standard having a conformity index for determining whether the image of the substrate and the reference image of an acceptable substrate are in conformity with each other.

9. The method of claim 7, wherein the soldering points being detected are formed by deposited metals deposed on the substrate during the manufacturing process.

10. The computerized system of claim 1, wherein said image processing device is designed to receive and process digital image signals representative of a planar surface.

11. The computerized system of claim 10, wherein said digital image signals of said planar surface are representative of the absence of a deposited metal on the soldering point.

* * * * *